(12) United States Patent
Stopper

(10) Patent No.: US 6,190,758 B1
(45) Date of Patent: Feb. 20, 2001

(54) NONWOVEN-FILM LAMINATES

(75) Inventor: Steven Ray Stopper, Duluth, GA (US)

(73) Assignee: Kimberly-Clark Worldwide, Inc., Neenah, WI (US)

( * ) Notice: Under 35 U.S.C. 154(b), the term of this patent shall be extended for 0 days.

(21) Appl. No.: 09/169,704

(22) Filed: Oct. 9, 1998

Related U.S. Application Data

(63) Continuation of application No. 08/883,011, filed on Jun. 26, 1997, now Pat. No. 5,900,306, and a continuation of application No. 08/432,889, filed on May 2, 1995, now abandoned.

(51) Int. Cl.[7] ........................................... B32B 27/14
(52) U.S. Cl. ........................ 428/198; 428/221; 442/394; 604/367
(58) Field of Search .................................. 604/367, 365, 604/366, 370; 428/220–222, 288, 349, 516, 198; 525/222; 442/394

(56) References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,855,046 | 12/1974 | Hansen et al. | 161/150 |
| 4,307,143 | 12/1981 | Meitner | 252/91 |
| 4,340,563 | 7/1982 | Appel et al. | 264/518 |
| 4,374,888 | 2/1983 | Bornslaeger | 428/198 |
| 4,410,582 | 10/1983 | Tsunashima et al. | 428/212 |
| 4,631,933 | 12/1986 | Carey, Jr. | 66/192 |
| 4,698,261 | 10/1987 | Bothe et al. | 428/201 |
| 4,741,957 | 5/1988 | Park | 428/349 |
| 4,769,261 | 9/1988 | Hazelton et al. | 428/35 |
| 4,818,600 | 4/1989 | Braun et al. | 428/290 |
| 4,865,908 | 9/1989 | Liu et al. | 428/248 |
| 4,876,156 | 10/1989 | Hwo | 428/516 |
| 4,880,706 | 11/1989 | Mazuera et al. | 428/516 |
| 4,891,957 | 1/1990 | Strack et al. | 66/192 |
| 4,956,232 | 9/1990 | Balloni et al. | 428/349 |
| 4,965,122 | 10/1990 | Morman | 428/225 |
| 4,965,123 | 10/1990 | Swan et al. | 428/314.4 |
| 4,981,747 | 1/1991 | Morman | 428/198 |
| 5,006,394 | 4/1991 | Baird | 428/138 |
| 5,087,667 | 2/1992 | Hwo | 428/222 |
| 5,091,236 | 2/1992 | Keller et al. | 428/213 |
| 5,108,820 | 4/1992 | Kaneko et al. | 428/198 |
| 5,108,827 | 4/1992 | Gessner | 428/219 |
| 5,114,781 | 5/1992 | Morman | 428/198 |
| 5,165,539 | 11/1992 | Weber et al. | 206/363 |
| 5,169,712 | 12/1992 | Tapp | 428/315.5 |
| 5,178,942 | 1/1993 | Frognet et al. | 428/317.9 |
| 5,250,343 | 10/1993 | Stewart | 428/141 |
| 5,271,883 | 12/1993 | Timmons et al. | 264/6 |
| 5,302,454 | 4/1994 | Cecchin et al. | 428/402 |
| 5,314,746 | 5/1994 | Johnson et al. | 428/338 |
| 5,318,842 | 6/1994 | Ogale | 428/349 |
| 5,326,625 | 7/1994 | Schuhmann et al. | 428/215 |
| 5,332,613 | 7/1994 | Taylor et al. | 428/152 |
| 5,336,552 | 8/1994 | Strack et al. | 428/224 |
| 5,368,927 | 11/1994 | Lesca et al. | 428/288 |
| 5,376,439 | 12/1994 | Hodgson et al. | 428/220 |
| 5,382,400 | 1/1995 | Pike et al. | 264/168 |
| 5,389,448 | 2/1995 | Schirmer et al. | 428/517 |
| 5,700,531 | * 12/1997 | Gillberg-Laforce . | |
| 5,900,306 | * 5/1999 | Stopper | 428/198 |

FOREIGN PATENT DOCUMENTS

| | | |
|---|---|---|
| 0 252 718 | 1/1988 | (EP) . |
| 0 309 073 | 3/1989 | (EP) . |
| 0 321 843 | 6/1989 | (EP) . |
| 0 400 333 | 12/1990 | (EP) . |
| 0 444 671 | 9/1991 | (EP) . |
| 0 472 946 | 3/1992 | (EP) . |
| 0 554 896 | 8/1993 | (EP) . |
| 0 600 246 | 6/1994 | (EP) . |
| 0604731 | * 7/1994 | (EP) . |
| 3 031 741 | 3/1978 | (JP) . |
| 3 063 484 | 6/1978 | (JP) . |
| 8 018 260 | 2/1983 | (JP) . |
| 1-047 535 | 2/1989 | (JP) . |
| 2-276 636 | 11/1990 | (JP) . |
| 4-224 943 | 8/1992 | (JP) . |
| 6-99556 | 4/1994 | (JP) . |

OTHER PUBLICATIONS

"Polymer Blends And Composites" by Manson, et al., copr. 1976 by Plenum Press, pp. 273–277.
Plastic Technology's Manufacturers Handbook & Buyer's Guide, 1994/95 from Bill Publications, p. 673.

\* cited by examiner

Primary Examiner—John G. Weiss
Assistant Examiner—David J. Cho
(74) Attorney, Agent, or Firm—Lisa J. Moyles; James B. Robinson; William D. Herrick

(57) ABSTRACT

There is provided herein a multilayer laminate comprised of a layer of a film and a layer of a nonwoven fabric. The film is made from polymers and has as one surface a semi-crystalline/amorphous or "heterophasic" polymer, an optional inner, less expensive, filler type polymer, and as the other surface, a polymer with a lower coefficient of friction. The nonwoven fabric may be a spunbond or meltblown fabric, preferably spunbond and preferably also including a heterophasic polymer. The film and nonwoven components are bonded together using thermal point bonding preferably while the film is stretched at least 5 percent. Such a laminate may be made into a personal care product like a diaper, training pant, absorbent underpants, adult incontinence product, and feminine hygiene product.

15 Claims, 2 Drawing Sheets

NONWOVEN-FILM LAMINATES

This application is a continuation of application Ser. No. 08/883,011 filed in the U.S. Patent and Trademark Office on Jun. 26, 1997, now U.S. Pat. No. 5,900,306, and application Ser. No. 08/432,889 filed in the U.S. Patent and Trademark Office on May 2, 1995 now abandoned each entitled "Nonwoven-Film Laminates.

BACKGROUND OF THE INVENTION

Thermoplastic resins have been extruded to form fibers, films and webs for a number of years. The most common thermoplastics for these applications are polyolefins, particularly polypropylene and polyethylene, though each material has its characteristic advantages and disadvantages vis a vis the properties desired in the final products.

Nonwoven fabrics are one type of product which can be made from such polymers and are useful for a wide variety of applications such as personal care products like diapers, feminine hygiene products and incontinence products, infection control products, garments and many others. The nonwoven fabrics used in these applications are often in the form of laminates having various numbers of layers of meltblown fabric, spunbond fabric and/or films like spunbond/meltblown/spunbond (SMS) laminates, SMMS laminates, spunbond/film (SF) and SFS laminates and even laminates having 6 or more layers.

One disadvantage to, in particular, SF laminates, is that they can delaminate under certain conditions. Such delamination is, of course, undesirable, as it can result in product failure. There remains a need for a spunbond/film laminate which is lightweight and thin yet also provides adequate adhesion between the layers such that delamination does not occur.

It is an object of this invention to provide laminates having at least one layer of a nonwoven fabric with at least one layer of a film where the laminate exhibits greater delamination or peel strength than heretofore known similar laminates.

SUMMARY OF THE INVENTION

There is provided herein a multilayer laminate comprised of a layer of a film and a layer of nonwoven fabric. The film is made from polymers and has as one surface a semi-crystalline/amorphous or "heterophasic" polymer, an optional inner, less expensive, filler type polymer, and as the other surface, a polymer with a lower coefficient of friction. The nonwoven fabric may be a spunbond or meltblown fabric, preferably spunbond and preferably also including a heterophasic polymer. The film and nonwoven components are bonded together using thermal point bonding preferably while the film is stretched at least 5 percent. Such a laminate may be made into a personal care product like a diaper, training pant, absorbent underpants, adult incontinence product, and feminine hygiene product.

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber. For example, the diameter of a polypropylene fiber given in microns may be converted to denier by squaring, and multiplying the result by 0.00629, thus, a 15 micron polypropylene fiber has a denier of about 1.42 ($15^2 \times 0.00629 = 1.415$).

As used herein the term "spunbonded fibers" refers to small diameter fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Levy, and U.S. Pat. No. 3,542,615 to Dobo et al. Spunbound fibers are generally not tacky when they are deposited onto a collecting surface. Spunbond fibers are generally continuous and have diameters larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin. Meltblown fibers are microfibers which may be continuous or discontinuous, are generally tacky when deposited onto a collecting surface.

As used herein the term "polymer" generally includes but is not limited to, homopolymers, copolymers, such as for example, block, graft, random and alternating copolymers, terpolymers etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein the term "heterophasic" in reference to a polymer means a thermoplastic polymer which has both elastic and plastic properties. Such polymers are sometimes referred to as "plasto-elastic" or "elastoplastic" polymers and may be semi-crystalline/amorphous in character. These polymers posses a comprise of elastic properties and mechanical resistance and can easily be transformed into manufactured articles by using the apparatus and processes normally used for thermoplastic materials.

As used herein the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, e.g. titanium dioxide for coloration, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "bioconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Conjugate and biconstituent fibers are also discussed in the textbook *Polymer Blends and Composites* by John a. Manson and Leslie H. Sperling, copyright 1976 by Plenum Press, a division of Plenum Publishing Corporation of New York, IBSN 0-306-30831-2, at pages 273 through 277.

As used herein the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "stitchbonded" means, for example, the stitching of a material in accordance with U.S. Pat. No. 4,891,957 to Strack et al. or U.S. Pat. No. 4,631,933 to Carey, Jr.

As used herein, "ultrasonic bonding" means a process performed, for example, by passing the fabric between a sonic horn and anvil roll as illustrated in U.S. Pat. No. 4,374,888 to Bornslaeger.

As used herein, "hydroentanglement" means a bonding process performed, for example, by subjecting a web to high pressure water jets which entangle fibers together and thereby increase web integrity.

As used herein "thermal point bond" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.0991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which as a bond area of about 16.9%. The C-Star pattern has cross-directional bar design interrupted by shooting stars. Other common patterns include a diamond pattern with repeating and slightly offset diamonds and a wire weave pattern looking as the name suggests, e.g. like a window screen. Typically, the percent bonding area varies from about 10% to around 30% of the area of the fabric laminate web. As in well known in the art, the spot bonding holds the laminate layers together as well as imparts integrity to each individual layer by bonding filaments and/or fibers within each layer.

As used herein, the term "bonding window" means the range of temperature of the calender rolls used to bond the nonwoven fabric together, over which such bonding is successful. For polypropylene spun bond, this bonding window is typically from about 270° F. to about 310° F. (132° C. to 154° C.). Below about 270° F. the polypropylene is not hot enough to melt and bond and above about 310° F. the polypropylene will melt excessively and can stick to the calender rolls. Polyethylene has an even narrower bonding window.

As used herein, the term "machine direction" or MD means the length of a fabric in the direction in which it is produced. The term "cross machine direction" or CD means the width of fabric, i.e. a direction generally perpendicular to the MD.

As used herein, the terms "necking" or "neck stretching" interchangeably refer to a method of elongating a nonwoven fabric, generally in the machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example in U.S. Pat. No. 4,443,513 to Meitner and Notheis, and U.S. Pat. Nos. 4,965,122, 4,981,747 and 5,114,781 to Morman.

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the terms "elastic" and elastomeric" when referring to a fiber, film or fabric mean a material which upon application of a biasing force, it stretchable to a stretched, biased length which is at least about 150 percent, or one and a half times, its relaxed, unstretched length, and which will recover at least 50 percent of its elongation upon release of the stretching, biasing force.

As used herein, the term "garment" means any type of non-medically oriented apparel which may be worn. This includes industrial work wear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein, the term "personal care product" means diapers, training pants, absorbent underpants, adult incontinence products, and feminine hygiene products. Such products generally have an outercover which is liquid penetration resistant and which also provides a visual barrier and is aesthetically pleasing. An outercover for a personal care product, e.g. a diaper, may also serve as a "landing area" or point of attachment for tape closure means and may provide an attachment means for hook and loop closure systems wherein the outercover material may be the hook or the loop means.

As used herein, the term "protective cover" means a cover for vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths and picnic area covers.

TEST METHODS

Melt Flow Rate: The melt flow rate (MFR) is a measure of the viscosity of a polymers. The MFR is expressed as the weight of material which flows from a capillary of known dimensions under a specified load or shear rate for a measured period of time and is measured in grams/10 minutes at 230° C. according to, for example, ASTM test 1238, condition E.

Peel test: In peel or delamination testing a laminate is tested for the amount of tensile force which will pull the layers of the laminate apart. Values for peel strength are obtained using a specified width of fabric, usually 4 inches (102 mm), clamp width and a constant rate of extension. The film side of the specimen is covered with masking tape or some other suitable material in order to prevent the film from ripping apart during the test. The masking tape is on only one side of the laminate and does not contribute to the peel strength of the sample. The sample is delaminated by and a sufficient amount to allow it to be clamped into position. The specimen is clamped in, for example, an Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154, which have 3 inch (76 mm) long parallel clamps. The sample specimen is then pulled apart at 180° of separation and the tensile strength recorded in grams.

DETAILED DESCRIPTION

Figure 1:
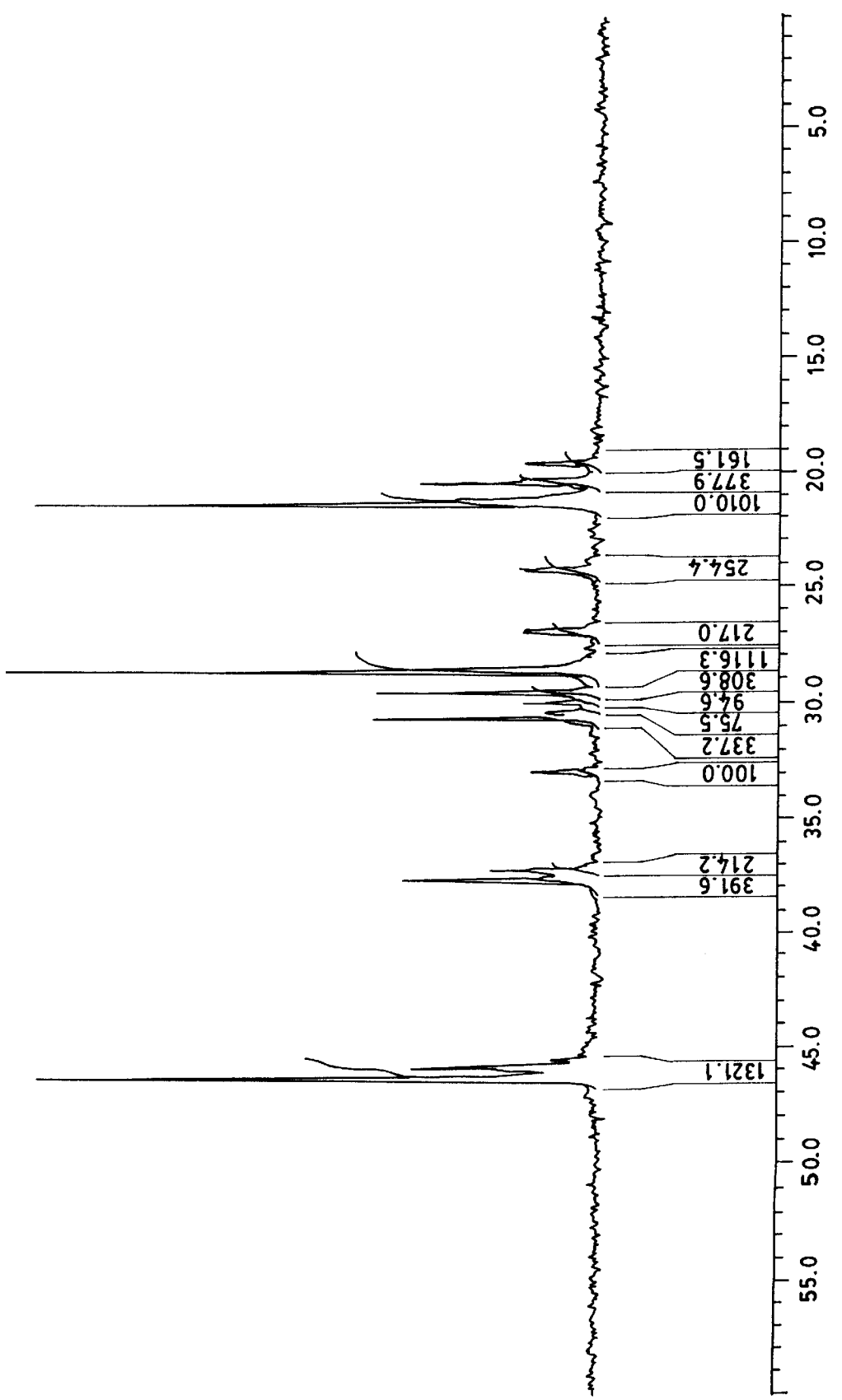
FIG. 1 is a graph of the carbon 13 Nuclear Magnetic Resonance (NMR) spectrum of Himont KS-050 with ppm from 0 to 60 as the horizontal axis and using tertiarymethylsilane as the carrier and performed in a manner known in the art on a Bruker AC-250 NMR spectrometer.

Thermoplastic polymers are useful in the production of films, fibers and webs for use in a variety of products such as personal care items, infection control products, garments and protective covers. One example of such a material is a film/nonwoven fabric laminate which functions as a liquid impervious retainer.

A film/nonwoven laminate may be used, for example, as a diaper outercover material. A diaper outercover material must perform the function of retaining bodily fluids and must also be aesthetically pleasing to the eye of the consumer, i.e., the material must look attractive to the eye and must also mask the view of the fluids and materials which the diaper is retaining. An outercover for a personal care product, e.g. a diaper, may also serve as a "landing area" or point of attachment for tape closure means and may also provide an attachment means for hook and loop closure systems wherein the outercover material may be the hook or the loop means. Such functionality requires that the laminate remain together without failure, an attribute which has been a problem for prior film/nonwoven laminates.

The inventor has discovered a way of achieving the result of a film/nonwoven laminate which will remain together as a laminate better than prior such materials. The instant invention uses a nonwoven fabric, preferably spunbond, component thermally bonded to a particular film. The film component is comprised of one surface layer which is made from a semi-crystalline/amorphous or "heterophasic" polymer and another surface layer which is preferably made from a lower coefficient of friction polymer. The film component also preferably has an inner layer of a less expensive polymer, like a polyolefin, to reduce overall cost. Pigments are also preferentially present in the inner layer.

The film component layers are extruded together using any method known in the art to be effective. The film component is produced in a thickness of from about 0.3 mils to about 0.8 mils. If three layers are present in the film component, i.e., the film component is an A/B/C coextruded film, it is preferred that the surface layers each be from about 3 to about 40 weight percent of the total component and that the inner layer contribute the balance. In one particular embodiment, the film component is extruded using an "A" layer which is a semi-crystalline/amorphous or heterophasic polymer in an amount of about 10 weight percent, a low coefficient of friction layer on the other outer surface or "C" layer in an amount of about 10 weight percent, and a polypropylene polymer in the "B" layer being the balance.

The "A" layer is made from polymers which are heterophasic in character. Suitable polymers are disclosed in European Patent Application EP 0444671 A3 (based on Application number 91103014.6), European Patent application EP 0472946 A2 (based on Application number 91112955.0), European Patent Application EP 0400333 A2 (based on Application number 90108051.5), U.S. Pat. No. 5,302,454 and U.S. Pat. No. 5,368,927. Other suitable heterophasic polymers include EnBA, ethylene/vinyl acetate copolymers, ethylene/methyl acetate copolymrs, EAA and other copolymers, and terpolymers of polypropylene, polyethylene and polybutylene as well as elastomers such as SEBS, SEPS, SBS, and urethanes which meet the definition of being heterophasic.

European Patent Application EP 0444671 A3 teaches a composition comprising first, 10–60 weight percent of a homopolymer polypropylene having an isotactic index greater than 90 or a crystalline copolymer of propylene with ethylene and/or other alpha-olefins containing more than 85 weight percent of propylene and having an isotactic index greater than 85; second, 10–40 weight percent of a copolymer containing prevailingly ethylene, which is insoluble in xylene at room temperature; and third, 30–60 weight percent of an amorphous ethylene-propylene copolymer, which is soluble in xylene at room temperature and contains 40–70 weight percent of ethylene, wherein the propylene polymer composition has a ratio between the intrinsic viscosities, in tetrahydronaphthalene at 135° C., of the portion soluble in xylene and of the portion insoluble in xylene at room temperature of from 0.8 to 1.2.

European Patent Application EP 0472946 A2 teaches a composition comprising first, 10–50 weight percent of a homopolymer polypropylene having an isotactic index greater than 80 or a crystalline copolymer of propylene with ethylene, a $CH_2=CHR$ alpha-olefin where R is a 2–8 carbon alkyl radical or combinations thereof, which copolymer contains more than 85 weight percent of propylene; second, 5–20 weight percent of a copolymer containing ethylene, which is insoluble in xylene at room temperature; and third, 40–80 weight percent of a copolymer fraction of ethylene and propylene or another $CH_2=CHR$ alpha-olefin, where R is a 2–8 carbon alkyl radical, or combinations thereof, and, optionally, minor portions of a diene, the fraction containing less than 40 weight percent of ethylene and being soluble in xylene at ambient temperature and having an intrinsic viscosity from 1.5 to 4 dl/g; where the percent by weight of the sum of the second and third fractions with respect to the total polyolefin composition is from 50 to 90 percent and the second to third fraction weight ratio being lower than 0.4.

European Patent Application EP 0400333 A2 teaches a composition comprising first, 10–60 weight percent of a homopolymer polypropylene having an isotactic index greater than 90 or a crystalline propylene copolymer with ethylene and/or a $CH_2=CHR$ olefin where R is a 2–8 carbon alkyl radical containing more than 85 weight percent of propylene and having an isotactic index greater than 85; second, 10–40 weight percent of a crystalline polymer fraction containing ethylene, which is insoluble in xylene at room temperature; and third, 30–60 weight percent of an amorphous ethylene-propylene copolymer containing optionally small proportions of a diene, which is soluble in xylene at room temperature and contains 40–70 weight percent of ethylene; where the composition has a flex modulus smaller than 700 MPa, tension set at 75 percent, less than 60 percent, tensile stress greater than 6 MPa and notched IZOD resilience at −20° and −40° C. greater than 600 J/m.

U.S. Pat. No. 5,302,454 teaches a composition comprising first, 10–60 weight percent of a homopolymer polypropylene having an isotactic index greater than 90 or of a crystalline propylene copolymer with ethylene with $CH_2=CHR$ olefin where R is a 2–6 carbon alkyl radical, or combinations thereof, containing more than 85 weight percent of propylene and having an isotactic index greater than 85; second, 10–40 weight percent of a crystalline polymer fraction containing ethylene and propylene, having an ethylene content of from 52.4 percent to about 74.6 percent and which is insoluble in xylene at room temperature; and third, 30–60 weight percent of an amorphous ethylene-propylene copolymer containing optionally small proportions of a diene, soluble in xylene at room temperature and contains 40–70 weight percent of ethylene; where the composition has a flex modulus smaller than 700 MPa, tension set at 75 percent, less than 60 percent, tensile stress greater than 6 MPa and notched IZOD resilience at −20° and −40° C. greater than 600 J/m.

U.S. Pat. No. 5,368,927 teaches a composition comprising first, 10–60 weight percent of a homopolymer polypropylene having an isotactic index greater than 80 or of a crystalline propylene copolymer with ethylene and/or an alpha-olefin having 5–10 carbon atoms, containing more than 85 weight percent of propylene and having an isotactic index greater than 80; second, 3–25 weight percent of an ethylene-propylene copolymer insoluble in xylene at room temperature; and third, 15–87 weight percent of a copolymer of ethylene with propylene and/or an alpha-olefin having 4–10 carbon atoms, and optionally a diene, containing 20–60 percent of ethylene, and completely soluble in xylene at ambient temperature.

Other polymers which may be used for the "A" layer include block copolymers such as polyurethanes, copolyether esters, polyamide polyether block copolymers, ethylene/vinyl acetates (EVA), block copolymers having the general formula A—B—A' or A–B like copoly(styrene/ethylene-butylene), styrene-poly(ethylene-propylene)-styrene, styrene-poly(ethylene-butylene)-styrene, (polystyrene/poly(ethylene-butylene)/polystyrene,poly(styrene/ethylene-butylene/styrene) and the like.

Useful resins include block copolymers having the general formula A—B—A' or A–B where A and A' are each a thermoplastic polymer endblock which contains a styrenic moiety such as a poly (vinyl arene) and where B is an elastomeric polymer midblock such as a conjugated diene or a lower alkene polymer. Block copolymers of the A—B—A' type can have different or the same thermoplastic block polymers for the A and A' blocks, and the present block copolymers are intended to embrace linear, branched and radial block copolymers. In this regard, the radial block copolymers may be designated $(A–B)_m$—X, wherein X is a polyfunctional atom or molecule and in which each (A—B)$_m$— radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A—B—A'" and "A–B" block copolymer, is intended to embrace all block copolymers having such rubbery blocks and thermoplastic blocks as discussed above, which can be extruded, and without limitation as to the number of blocks. The film may be formed from, for example, (polystyrene/poly(ethylene-butylene)/polystyrene) block copolymers. Commercial examples of such copolymers are, for example, those known as KRATON® materials which are available from Shell Chemical Company of Houston, Tex. KRATON® block copolymers are available in several different formulations, a number of which are identified in U.S. Pat. Nos. 4,663,220 and 5,304,599, hereby incorporated by reference.

Polymers composed of an A—B—A—B tetrablock copolymer may also be used in the practice of this invention. Such polymers are discussed in U.S. Pat. No. 5,332,613 to Taylor et al. In such polymers, a is a thermoplastic polymer block and B is an isoprene monomer unit hydrogenated to substantially a poly(ethylene-propylene) monomer unit. An example of such a tetrablock copolymer is a styrene-poly (ethylene-propylene)-styrene-poly(ethylene-propylene) or SEPSEP block copolymer available from the Shell Chemical Company of Houston, Tex. under the trade designation KRATON® G-1657.

Other exemplary materials which may be used include polyurethane materials such as, for example, those available under the trademark ESTANE® from B. F. Goodrich & Co. or MORTHANE® from Morton Thiokol Corp., polyamide polyether block copolymer such as, for example, that known as PEBAX® available from Atochem Inc. Polymers Division (RILSAN®), of Glen Rock, N.J. and polyester materials such as, for example, those available under the trade designation HYTREL® from E. I. DuPont De Nemours & Company.

Suitable polymers also include copolymers of ethylene and at least one vinyl monomer such as, for example, vinyl acetates, unsaturated aliphatic monocarboxylic acids, and esters of such monocarboxylic acids. These copolymers are disclosed in, for example, U.S. Pat. No. 4,803,117.

Particularly suitable polymers for the "A" layer are available commercially under the trade designation "CATALLOY polymer" from the Himont Chemical Company of Wilmington, Del. Specific commercial examples are CATALLOY® polymer KS-084P and CATALLOY® polymer KS-057P. Himont's KS-057P has a melt flow rate of 30 and a density of 0.9 gm/cc, according to page 673 of *Plastic Technology's Manufacturers Handbook & Buyer's Guide*, 1994/95 from Bill Publications, 355 Park Ave. South, N.Y., N.Y., 10010.

Figure 2:
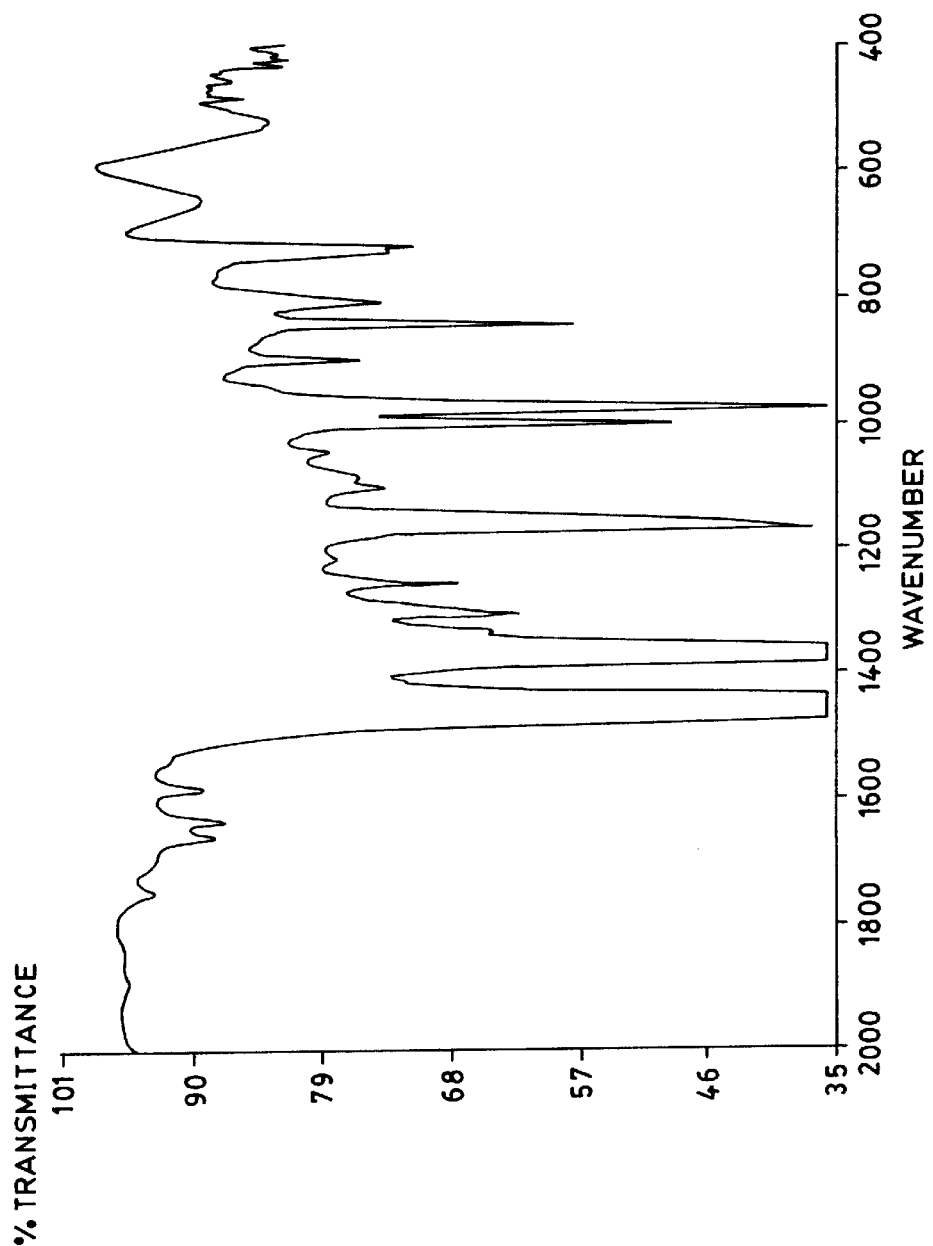
FIG. 2 is a graph of the infrared (IR) scan or curve of Himont KS-050 random block copolymer having wavenumber from 400 to 2000 as the horizontal axis and percent transmittance from 35 to 101 as the vertical axis.

Polymers can be characterized in a number of ways, two of which being the nuclear magnetic resonance scan (NMR) and the infrared scan (IR). FIGS. 1 and 2 show these scans of a heterophasic polymer preferred in the practice of this invention, Himont's KS-050, prior to peroxide cracking to produce KS-057P. Peroxide cracking is a process for raising the melt flow rate of a polymer and an example of such a procedure is taught in U.S. Pat. No. 5,271,83 to Timmons.

The NMR spectrum and IR curve of the polymer show that KS-057P has about 3 percent random ethylene molecules and about 9–10 percent block ethylene molecules.

The "B" layer may be a polypropylene polymer or copolymer. Since this layer is relatively thick, the majority of opacity may be added to this layer. Opacity may be added through the use of, for example, $TiO_2$ or $CaCO_3$. Commercially available opacity increasers are, for example, Techmer's PM 18074 E $TiO_2$ concentrate and Standridge Chemical Company's SCC 13602 $TiO_2$ concentrate. These concentrates are approximately 70 percent of Dupont's $TiO_2$ in a carrier of 30 percent LDPE.

The "C" layer provides the other surface to the film. It is important that the C layer have a lower coefficient of friction than the A layer for ease of winding, unwinding and film handling through the production steps for converting the film/nonwoven laminate into a final product like a diaper. This may be accomplished by including a large proportion of polypropylene in this layer. Typical polypropylenes which may be used are Exxon Chemical Company's ESCORENE® polypropylene 3445 or Shell Chemical Company's E5D47.

The various film layers may also have small amounts of additives present to improve processibility such as low density polyethylene (LDPE) like those available from Quantum Chemical Company under the designation NA 334 or those available from Rexene under the designation 1058 LDPE. Many similar LDPE polymers are commercially available.

The nonwoven fabric component of this invention is preferably spunbond material and preferably between about 0.3 to 1 osy (11 gsm to 34 gsm). The polymers which may be used to produce the spunbond component are thermoplastic polymer such as polyolefins, polyamides, and polyesters, preferably polyolefins and still more preferably a blend including a heterophasic polymer in an amount up to about 50 weight percent. More particularly, the nonwoven fabric may be comprised of a blend of polypropylene like Exxon Chemical Company's ESCORENE® polypropylene 3445 of Shell Chemical Company's E5D47, and about 40 weight percent of a heterophasic polymer like CATALLOY® polymer KS-057P. Still more particularly, the nonwoven fabric may be comprised of a blend of high crystalline polypropylene and about 20 weight percent CATALLOY® polymer KS-057P.

The nonwoven component and the film component are bonded together using thermal point bonding preferably after the film is stretched approximately 60 to 65 percent in the machine direction. This stretching and joining may be performed according to U.S. patent application Ser. No. 07/997,800 and European Patent Application EP 0604731 A1 (based on Application number 93117426.2) and commonly assigned to assignee of record, Kimberly-Clark Corporation. Briefly, this procedure involves extending a first extensible layer from an original length to an expanded length with the expanded length being at least 5 percent greater than the original length. Depending upon the degree of stretching, the first extensible layer may be permanently deformed. Next, a second layer of material is placed in juxtaposition with the first layer while the first layer is still in the expanded length and the two layers are then attached to one another at a plurality of spaced-apart bond sites to form the laminate which includes a plurality of bonded and unbonded areas. Once the laminate has been formed, the first layer is allowed to relax to a third length which is usually longer than the first length of the first layer. As a result of the attachment of the second layer to the first layer while the first layer is in an expanded state, once the laminate contracts, the first layer gathers and puckers, thereby forming a much bulkier material as compared to a simple non-stretched laminate of the same two materials. Generally, stretching is performed by winding the film around a number of rollers, with later rollers running at a higher speed than that of earlier rollers, resulting in a stretching and thinning of the film. Such stretching may reduce the film thickness by about a third or more. For example, a film according to this invention may be produced which has a thickness of 0.6 mil prior to stretching and 0.4 mil after stretching.

In addition, a compatible tackifying resin may be added to the extrudable compositions described above to provide tackified materials that autogenously bond. Any tackifier resin can be used which is compatible with the polymers and can withstand the high processing (e.g., extrusion) temperatures. If the polymer is blended with processing aids such as, for example, polyolefins or extending oils, the tackifier resin should also be compatible with those processing aids. Generally, hydrogenated hydrocarbon resins are preferred tackifying resins, because of their better temperature stability. REGALREZ™ and ARKON™ P series tackifiers are examples of hydrogenated hydrocarbon resins. REGAL-REZ™ hydrocarbon resins are available from Hercules Incorporated. ARKON™ P series resins are available from Arakawa Chemical (U.S.A.) Incorporated. The tackifying resins such as disclosed in U.S. Pat. No. 4,787,699, hereby incorporated by reference, are suitable. Other tackifying resins which are compatible with the other components of the composition and can withstand the high processing temperatures, can also be used.

The nonwoven component of the laminates of this invention may be produced by the meltblowing or spunbonding processes which are well known in the art. These processes generally use an extruder to supply melted thermoplastic polymer to a spinnerette where the polymer is fiberized to yield fibers which may be staple length or longer. The fibers are then drawn, usually pneumatically, and deposited on a moving foraminous mat or belt to form the nonwoven fabric. The fibers produced in the spunbond and meltblown processes are microfibers as defined above.

In order to illustrate the advantages of laminates according to this invention, the following Examples and Controls were developed. All laminates were thermally bonded using a 240° F. (11620 C.) pattern roll and a 200° F. (93° C.) anvil roll.

CONTROL

An A/B/A type film was stretch thinned from 0.6 to 0.4 mil and thermally laminated with a C-Star bond pattern to a 0.5 osy (17 gsm) polypropylene spunbond layer made from ESCORENE® polypropylene 3445. The film layers had a ratio of 30/40/30. The "A" layer was made of 65 percent of Himont's CATALLOY® polymer 71-1, 25 percent of Exxon's 3445, 5 percent of low density polyethylene (Quantum Chemical's NA 334) and 5 percent of $TiO_2$ concentrate (Ampacet 110210, 50/50 blend in polypropylene). The "B" layer was made of 25 percent of Himont's CATALLOY® polymer 71-1, 30 percent of Exxon's 3445, 5 percent of low density polyethylene (Quantum Chemical's NA 334) and 40 percent of $TiO_2$ concentrate.

EXAMPLE 1

An A/B/C type film was stretch thinned from 0.6 to 0.4 mil and thermally laminated with a C-Star bond pattern to a 0.5 osy (17 gsm) polypropylene spunbond layer made from ESCORENE® polypropylene 3445. The film layers had a ratio of 10/80/10. The "A" layer was made of 85 percent of Himont's CATALLOY® polymer KS-084P, 10 percent of Exxon's 3445, and 5 percent of Quantum Chemical's NA 334 LDPE. The "B" layer was made of 0 percent of Himont's CATALLOY® polymer KS-084P, 43 percent of Exxon's 3445, and 17 percent of $TiO_2$ concentrate available from the Standridge Chemical Company of Social Circle, Georgia under the trade designation SCC 13602. The "C" layer was made of 35 percent of Himont's CATALLOY® polymer KS-084P, 60 percent of Exxon's 3445, and 5 percent of Quantum Chemical's NA 334 LDPE.

EXAMPLE 2

An A/B/C type film was stretch thinned from 0.6 to 0.4 mil and thermally laminated with a C-Star bond pattern to a 0.5 osy (17 gsm) polypropylene spun bond layer made from ESCORENE® polypropylene 3445. The film layers had a ratio of 10/80/10. The "A" layer was made of 93 percent of Himont's CATALLOY® polymer KS-084P and 5 percent of Rexene Chemical's 1058 LDPE. The "B" layer was made of 40 percent of Himont's CATALLOY® polymer KS-084P, 43 percent of Exxon's 3445, and 17 percent of $TiO_2$ concentrate available from the Techmer Company under the trade designation PM 18074E. The "C" layer was made of 40 percent of Himont's CATALLOY® polymer KS-084P, 55 percent of Exxon's 3445, and 5 percent of Rexene's 1058 LDPE.

The Control and Examples were tested for delamination according to the peel test described above and the results are given in Table 1.

TABLE 1

| Sample | 180° Peel Strength |
| --- | --- |
| Control | 60–70 grams |
| Example 1 | 120–130 grams |
| Example 2 | 126–142 grams |

The Table shows that the unique combination of film layers of this invention improves peel strength significantly, to more than 120 grams. This is an important advance in the technology of personal care products and will produce more durable and aesthetically pleasing products for the consumer.

What is claimed is:

1. A film/nonwoven laminate comprising:
   a first component which is a multi-layer film comprising a first surface layer of a heterophasic polymer and a second surface layer of a polymer having a lower coefficient of friction than said first surface layer, and said first component further comprising an interior layer between said surface layers comprising a polyolefin, wherein said interior layer contains opacity increasers; and
   a second component which is a nonwoven fabric having at least one layer, wherein said first and second components are bonded together by thermal point bonding and said laminate has a 180° peel strength of at least 120 grams.

2. The laminate of claim 1 wherein said first surface layer of said heterophasic polymer is thermally bonded and located next to said second component to form said laminate.

3. The laminate of claim 2 wherein said film is stretched at least 5 percent prior to said thermal bonding.

4. The laminate of claim 1 wherein said first component further comprises as said first and second surface layers from 10 to 80 weight percent of said first component and as said interior layer from 20 to 90 weight percent of said first component.

5. The laminate of claim 1 wherein said second component comprises a spunbond thermoplastic polymer web.

6. The laminate of claim 5 wherein said polymer web comprises a heterophasic polymer.

7. The laminate of claim 5 wherein said second component comprises at least one heterophasic polymer.

8. A personal care product selected from the group consisting of diapers, training pants, absorbent underpants, adult intontinence products, and feminine hygiene products including an outercover comprises of the laminate of claim 1.

9. The personal care product of claim 8 which is a diaper.

10. The personal care product of claim 8 which is an absorbent underpant.

11. The personal care product of claim 8 which is an adult incontinence product.

12. The personal care product of claim 8 which is a feminine hygiene product.

13. A film/nonwoven laminate comprising:
   a first component which is a multi-layer film comprising a first surface layer of a heterophasic polymer and a second surface layer of a polymer having a lower coefficient of friction than said first surface layer;

a second component which is a nonwoven fabric having at least one layer, wherein said first and second components are bonded together by thermal point bonding and said laminate has a 180 degree peel strength of at least 120 grams.

14. A film/nonwoven laminate as defined in claim 13, wherein said second surface layer of said first component comprises polypropylene.

5. A film/nonwoven laminate as defined in claim 13, wherein said first component is stretched at least 5 percent prior to being thermal bonded to said second component.

* * * * *

UNITED STATES PATENT AND TRADEMARK OFFICE
CERTIFICATE OF CORRECTION

PATENT NO. : 6,190,758 B1
DATED : February 20, 2001
INVENTOR(S) : Steven Ray Stopper It is certified that error appears in the above-identified patent and that said Letters Patent is hereby corrected as shown below:

Column 2,
Line 58, "comprise" should read -- compromise --;
Line 42, after "are generally" should read -- smaller than 10 microns in diameter, and are --;
Line 48, "terpolymers etc." should read -- terpolymers, etc. --;

Column 3,
Line 36, "John a. Manson" should read -- John A. Manson --;
Line 61, "bond" should read -- bonding --;

Column 4,
Line 15, "(0.0991 mm)" should read -- (0.991 mm) --;
Line 35, "spun bond" should read -- spunbond --;
Line 57, "for example" should read -- for example, --;

Column 5,
Line 13, "non-medically" should read -- nonmedically --;

Column 6,
Line 67, "European Patent application" should read -- European Patent Application --;

Column 8,
Line 19, "5 - 10" should read -- 4 - 10 --;

Column 9,
Line 4, "a is a" should read -- A is a --;
Line 44, "5,271,83" should read -- 5,271,883 --;

Column 10,
Line 18, "3445 of shell" should read -- 3445 or shell --;
Line 28, "U.S. patent application" should read -- U.S. Patent Application --;

Column 11,
Line 1, after "resins"." should read -- Zonatac™ 501 lite is an example of a terpene hydrocarbon. --;
Line 27, "A/B/A/" should read -- A/B/C --;
Line 48, "of 0 percent" should read -- of 40 percent --;

Column 12,
Line 55, "intontinence" should read -- incontinence --;
Line 56, "comprises" should read -- comprised --;

UNITED STATES PATENT AND TRADEMARK OFFICE
CERTIFICATE OF CORRECTION

PATENT NO. : 6,190,758 B1
DATED : February 20, 2001
INVENTOR(S) : Steven Ray Stopper It is certified that error appears in the above-identified patent and that said Letters Patent is hereby corrected as shown below:

Column 14,
Line 4, "5" should read -- 15 --;

Signed and Sealed this

Twenty-seventh day of November, 2001

Attest:

*Attesting Officer*

NICHOLAS P. GODICI
*Acting Director of the United States Patent and Trademark Office*